(12) United States Patent
Nunez

(10) Patent No.: US 8,747,485 B1
(45) Date of Patent: Jun. 10, 2014

(54) ARTIFICIAL ANKLE JOINT

(76) Inventor: Rene Nunez, Lawton, OK (US)

( * ) Notice: Subject to any disclaimer, the term of this patent is extended or adjusted under 35 U.S.C. 154(b) by 169 days.

(21) Appl. No.: 13/200,888

(22) Filed: Oct. 4, 2011

(51) Int. Cl.
*A61F 2/66* (2006.01)

(52) U.S. Cl.
USPC .......................................................... 623/49

(58) Field of Classification Search
USPC .......................................................... 623/49
See application file for complete search history.

(56) References Cited

U.S. PATENT DOCUMENTS

| | | | | |
|---|---|---|---|---|
| 3,851,337 | A | * | 12/1974 | Prahl ................................. 623/49 |
| 3,982,280 | A | * | 9/1976 | Asbelle et al. ................... 623/49 |
| 5,037,443 | A | | 8/1991 | Haupt |
| 5,425,780 | A | * | 6/1995 | Flatt et al. ........................ 623/38 |
| 5,443,527 | A | * | 8/1995 | Wilson ............................. 623/49 |
| 6,228,124 | B1 | | 5/2001 | Slemker et al. |
| 6,712,860 | B2 | | 3/2004 | Rubie et al. |
| 6,764,521 | B2 | * | 7/2004 | Molino et al. ................... 623/52 |
| 7,951,101 | B2 | | 5/2011 | Pusch |
| 2004/0225375 | A1 | * | 11/2004 | Chen ................................ 623/38 |
| 2007/0255427 | A1 | * | 11/2007 | Kloos et al. ...................... 623/48 |
| 2008/0119933 | A1 | * | 5/2008 | Aebi et al. .................. 623/17.16 |

OTHER PUBLICATIONS

Plantarflexion, en.wikipedia.org/wiki/Plantarflexion, Jun. 23, 2011, pp. 2.
Foot Types, cfhc.ca/health.html, Jun. 23, 2011, pp. 6.
Anatomical terminology, en.wikiversity.org/wiki/Anatomical_Terminology, Jun. 23, 2011, pp. 3.
Dorsiflexion, answers.com/topic/dorsiflexion, Jun. 23, 2011, pp. 3.
Plantarflexion, merriam-webster.com/medical plantar%20flexion, Jul. 12, 2011, pp. 1.
Dorsiflexion, merriam-webster.com/medical dorsiflexion, Jul. 12, 2011, pp. 1.
Clevis, goole.com/, Jul. 13, 2011, pp. 2.
Transverse plane, en.wikipedia.org/wiki/Transverse_plane, Jul. 14, 2011, pp. 2.
Anatomical Planes of the Body, spineuniverse.com/anatomical/anatomical-planes-body, Jul. 14, 2011, pp. 4.
Universal joint, bing.com/Dictionary/search, Sep. 16, 2011, pp. 1.
Universal joint, en.wikipedia.org/wiki/Universal_joint, Sep. 16, 2011, pp. 2.

\* cited by examiner

*Primary Examiner* — Bruce E Snow
*Assistant Examiner* — Melissa Hoban
(74) *Attorney, Agent, or Firm* — Thomas R. Weaver

(57) ABSTRACT

An artificial ankle joint having a universal joint and shock absorbers is provided. The artificial ankle joint enables distribution of vertically applied weight of a human body to ground, and enables an artificial foot connected to the artificial ankle joint to move in multiple axial directions.

11 Claims, 6 Drawing Sheets

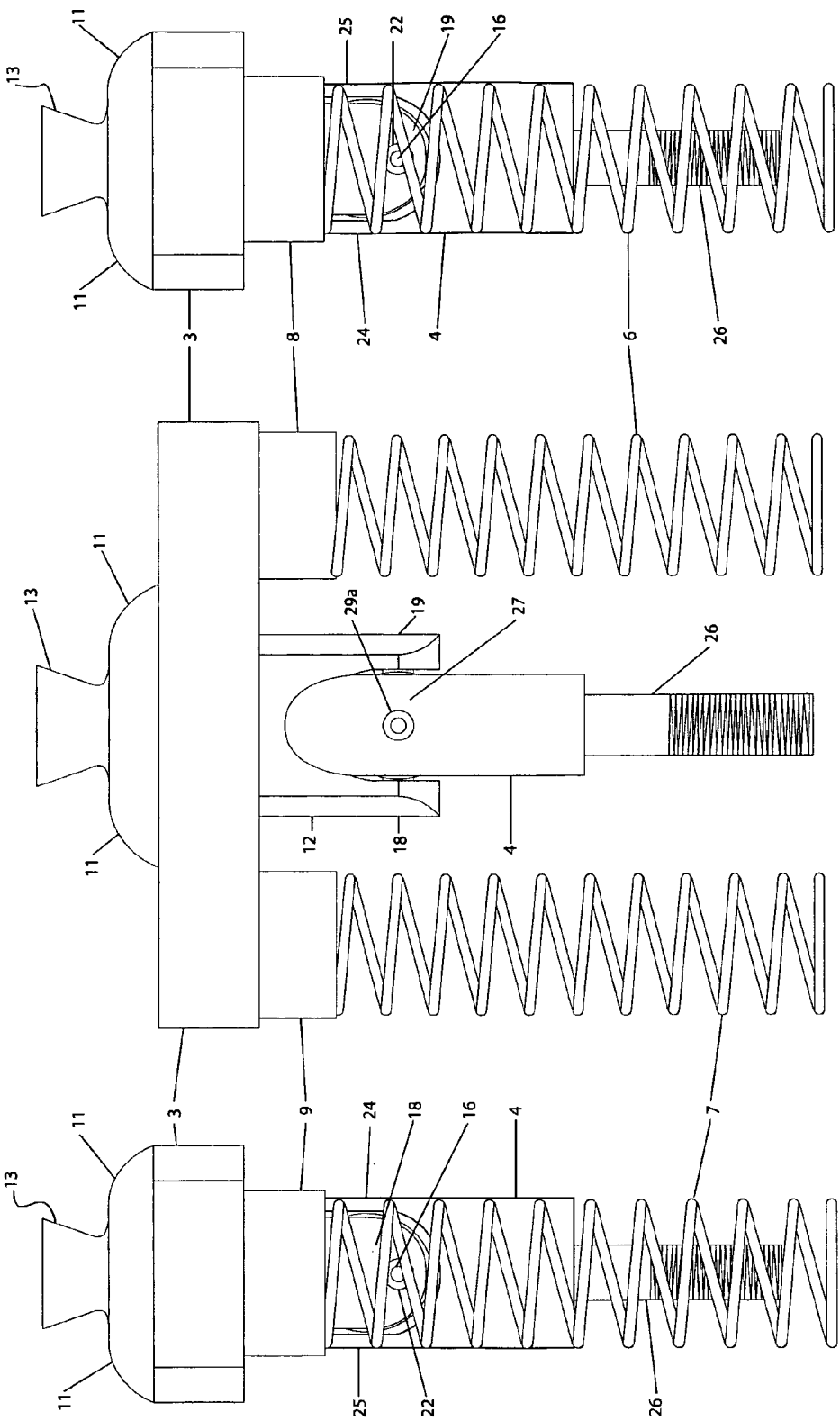

ARTIFICIAL ANKLE JOINT

BACKGROUND OF THE INVENTION

1. Technical Field of the Invention

This invention relates to a prosthetic device for a human being. The invention further relates to an artificial ankle joint, referred to herein as an artificial ankle. The invention still further relates to an artificial ankle which operates to enable an artificial foot to move in multiple axial directions.

2. Description of the Prior Art and Problems Solved

It is known that a person who loses a foot and an ankle can employ a prosthetic device to replace the lost foot and ankle to thereby enable the person to stand in an erect position and to walk without extrinsic assistance, such as by use of a cane or a crutch.

It is known that a natural ankle receives the weight of the body transmitted to it by the bones of the lower leg, i.e., the tibia and the fibula, and then distributes the weight to the sole of the foot and ultimately to ground. A problem encountered in the use of an artificial ankle and foot involves the capability of the combination to dampen and/or to absorb shock caused by forces generated by the weight of the body and then to distribute the weight to ground.

It is known that a natural ankle enables a foot to move to a toe down-heel up position, and to a toe up-heel down position. In geometric terms, the toe down position increases the angle between the front of the foot and the leg, and the toe up position decreases the angle between the front of the foot and the leg. These movements in a natural ankle are produced by rotation of the foot in a first vertical plane around a first horizontal axis which passes through the ankle and which is perpendicular to the first vertical plane. The first vertical plane, in anatomical terminology, is called a sagittal plane and is sometimes referred to as a para sagittal plane. A specific sagittal plane, called the mid-sagittal plane, or the median plane, divides the body into right and left halves. Accordingly, for purposes of this disclosure, the sagittal plane which passes through the ankle is parallel to the median plane and divides the foot into right and left halves. The toe down-heel up position is referred to as plantar flexion, and the toe up-heel down position is referred to as dorsiflexion. The bottom of the foot, the sole, is referred to as the plantar, and the top of the foot is referred to as the dorsum or dorsal. Accordingly, another problem encountered in the use of the combination of an artificial ankle and an artificial foot is the capability of the artificial foot to produce plantar flexion and dorsiflexion.

It is known that a natural ankle enables a foot to move in left and right directions. Such movement in a natural ankle is produced by rotation of the foot in a second vertical plane around a second horizontal axis which passes through the ankle and which is perpendicular to the second vertical plane. The second vertical plane, in anatomical terminology, is called a frontal or a coronal plane. A coronal plane of interest herein divides the foot into a front portion, the toe end, and a rear portion, the heel end. The anatomical terms for the left and right movements depend upon the direction of the movement of the foot with regard to the previously mentioned median plane. Movement of the sole of the foot, the plantar, away from the median plane is called eversion, and movement of the sole of the foot, the plantar, towards the median plane is called inversion. Accordingly, still another problem encountered in the use of the combination of an artificial ankle and an artificial foot is the capability of the artificial foot to produce eversion and inversion.

The above mentioned first and second vertical planes are perpendicular each to the other. The intersection of the first and second vertical planes is a vertical line which passes through the ankle, and is, therefor, the line of action through which the weight of the body passes from the tibia and the fibula to the foot and ultimately to ground.

In addition to the intersecting first and second vertical planes, a horizontal plane, referred to as a transverse plane or an axial plane, also passes through the ankle and is perpendicular to each of the first and second vertical planes. The line of intersection of the first vertical plane and the horizontal plane is the above mentioned second horizontal axis. The second horizontal axis accordingly lies in the horizontal plane and the first vertical plane. The line of intersection of the second vertical plane and the horizontal plane is the above mentioned first horizontal axis. The first horizontal axis accordingly lies in the horizontal plane an the second vertical plane. The first and second horizontal axes are perpendicular each to the other and intersect at a point in the center of the ankle.

There is a need for an artificial foot having an artificial ankle with sufficient flexibility to permit distribution of vertically applied weight of the body, and to enable the artificial foot to produce plantar flexion, dorsiflexion, eversion and inversion.

SUMMARY OF THE INVENTION

This invention provides an artificial ankle which enables an artificial foot to move in multiple axial directions. Accordingly, the combination of an artificial foot and the artificial ankle of this invention enables distribution of vertically applied weight of the body to ground, and also enables rotational motions of the foot to produce plantar flexion, dorsiflexion, eversion and inversion.

The invention is an article of manufacture broadly comprised of an artificial ankle, further comprised of an artificial ankle and an artificial foot and still further comprised of an artificial ankle, an artificial foot and a pylon, wherein the artificial ankle is situated intermediate the artificial foot and the pylon.

The artificial ankle has a top side, a bottom side, a front end and a rear end. The top side of the ankle is adapted for connection to the pylon, and the bottom side of the ankle is adapted for connection to the top side of the artificial foot.

The artificial ankle is comprised of a universal joint and further comprised of a bridge, a universal joint, a clevis and shock absorbers. For purposes of this disclosure, a universal joint is a coupling which connects rotatable shafts which are in line with each other, wherein the universal joint permits rotation in at least two, and up to three planes. A universal joint can be defined as a joint or coupling in a rigid rod that allows the rod to "bend" in any direction, and is commonly used in shafts that transmit rotary motion. It consists of a pair of hinges located close together, oriented at 90 degrees to each other and connected by a cross shaft.

The bridge includes a boss and a shackle, wherein the boss is rigidly positioned on the top side of the bridge and the shackle is rigidly positioned on the bottom side of the bridge. The shackle is representative of a rod which is connected to one of the pair of hinges in the universal joint. The clevis is representative of a rod which is connected to the second of the pair of hinges in the universal joint. The universal joint useful herein thus features rotatable connections to a shackle and rotatable connections to a clevis, wherein the connections are separated at 90 degree intervals. The mode of coupling the shackle and the clevis by means of the universal joint, as disclosed in this invention, enables the clevis to rotate in the sagittal plane around the first horizontal axis (to thereby produce plantar flexion and dorsiflexion), and enables the clevis to rotate in the frontal plane around the second horizontal axis (to thereby produce eversion and inversion). The universal joint further enables rotation of the clevis in a third plane which such rotation is a combination of rotation in the sagittal plane and the frontal plane.

In one embodiment, the universal joint can be a pair of perpendicularly opposed connected axles, wherein one of the pair of axles is rotatably attached to the shackle and the second of the pair of axles is rotatably attached to the clevis.

In another embodiment, the universal joint is a ball wherein the shackle is rotatably attached to a first axle extending from opposite sides of the ball and the clevis is rotatably attached to a second axle extending from opposite sides of the ball. The first axle and the second axle each lie in the same plane and are perpendicular each to the other. For purposes of this disclosure, the universal joint in the form of the described ball is referred to as a ball joint.

In one embodiment, the artificial ankle includes two shock absorbers positioned on the bottom of the bridge. In this regard, the bottom of the bridge includes pockets for retaining the shock absorbers, which can be coil springs, in operating contact with the bridge. The coil springs are identical wherein the first spring is positioned in a first sleeve inserted in a first pocket on the bottom-front of the bridge, and the second spring is positioned in a second sleeve inserted in a second pocket on the bottom-rear of the bridge. The shackle is intermediate the first pocket and the second pocket.

The clevis, in addition to being rotatably attached to the universal joint, is adapted for connecting the ankle to the foot.

In the neutral position, as defined below, the boss, the shackle, the universal joint and the clevis are in substantial vertical alignment, and the shackle, the clevis, the universal joint and shock absorbers are in substantial horizontal alignment.

DESCRIPTION OF THE DRAWINGS

FIG. 4 is the end view of the clevis of the artificial ankle and illustrates the connection of the clevis to the ball joint.

FIG. 5 is a side view of the assembled components of FIG. 3.

FIG. 6 is the front view of FIG. 5.

FIG. 7 is the rear view of FIG. 5.

DESCRIPTION OF THE INVENTION

Figure 1:
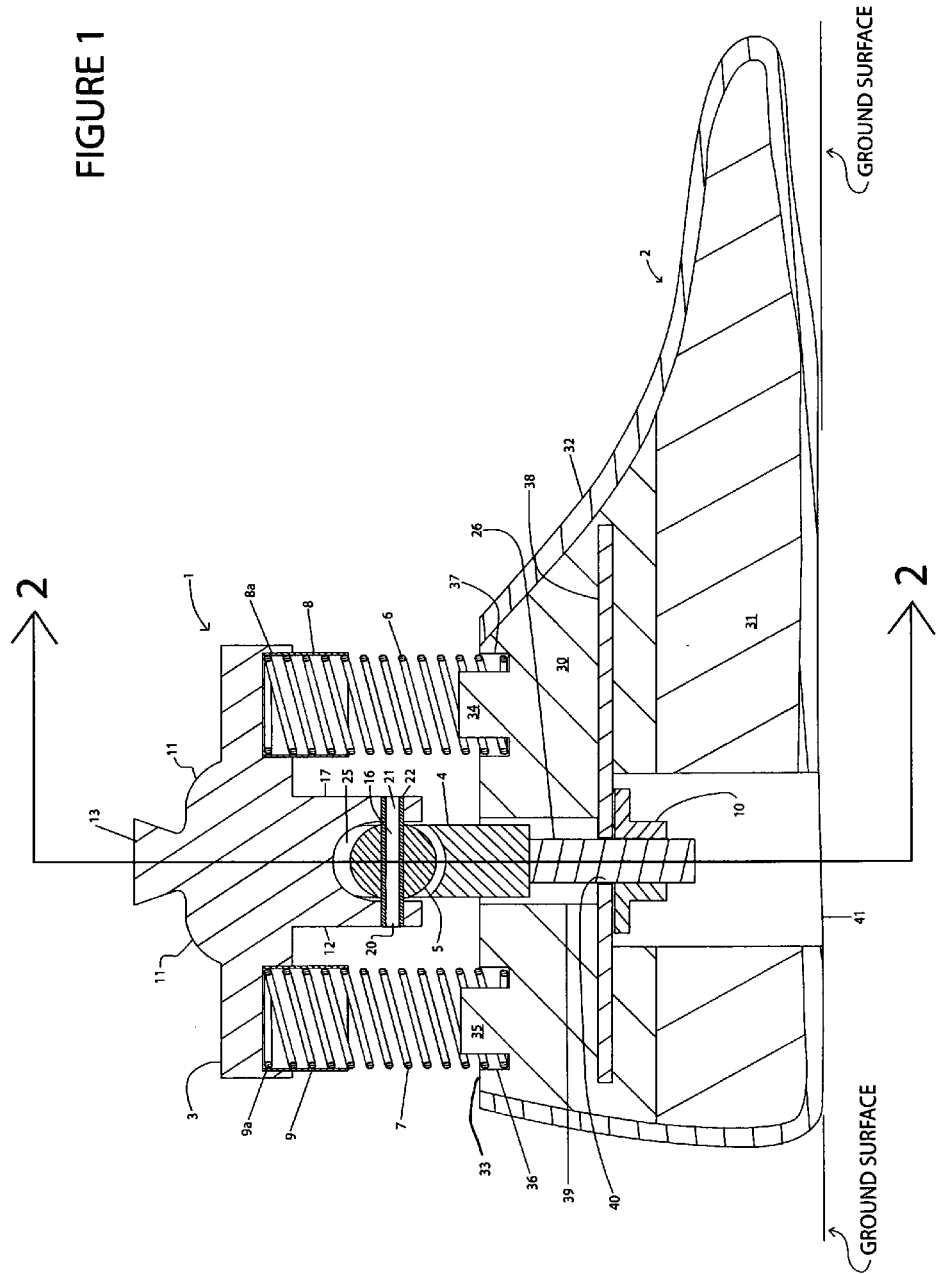
FIG. 1 is a cross sectional side view of the artificial foot of this invention in operating connection with the artificial ankle of this invention. The section is illustrated in a sagittal plane which passes through the ball joint, wherein the front of the foot, the toe end, is situated to the right of the ball joint and the rear of the foot, the heel end, is situated to the left of the ball joint.
Figure 2:
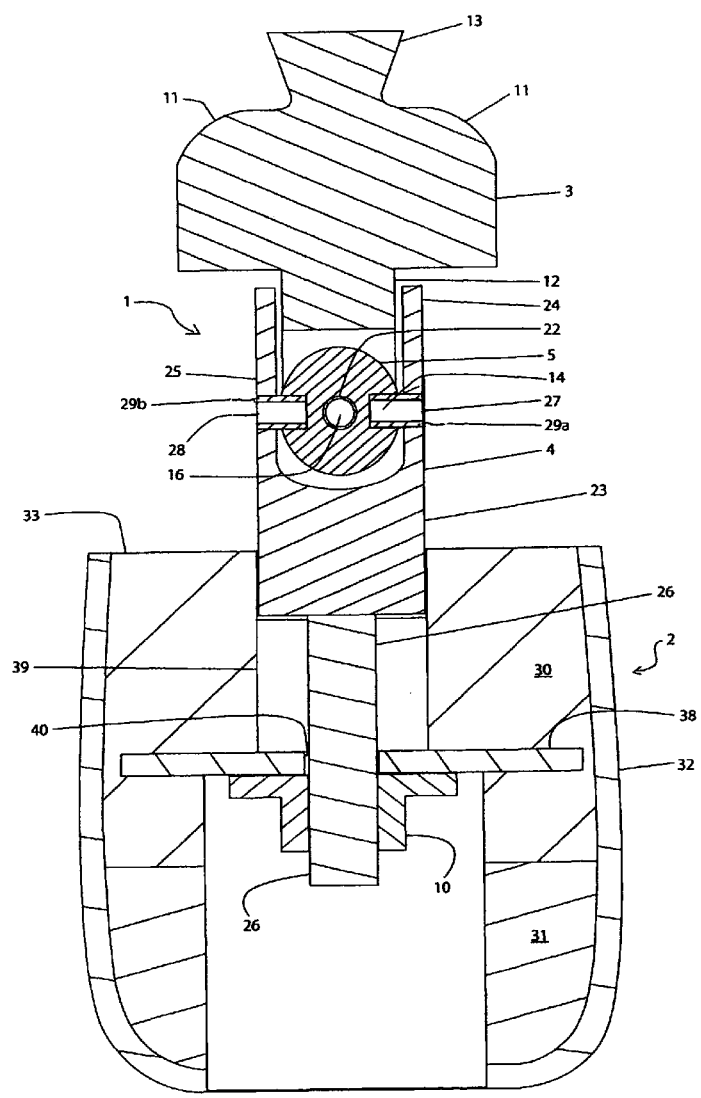
FIG. 2 is a cross sectional end view of the artificial foot of this invention taken in the direction of cut line 2-2 of FIG. 1. The section is illustrated in a frontal plane which passes through the ball joint and shows the artificial foot in operating connection with the artificial ankle of this invention.

FIGS. 1 and 2 illustrate the article of manufacture of this invention comprised of artificial ankle 1 in operating connection with artificial foot 2. The combination of ankle 1 and foot 2 is shown to be in the neutral position, that is, the combination is not in plantar flexion nor in dorsiflexion and is not in eversion position nor in inversion position.

Figure 3:
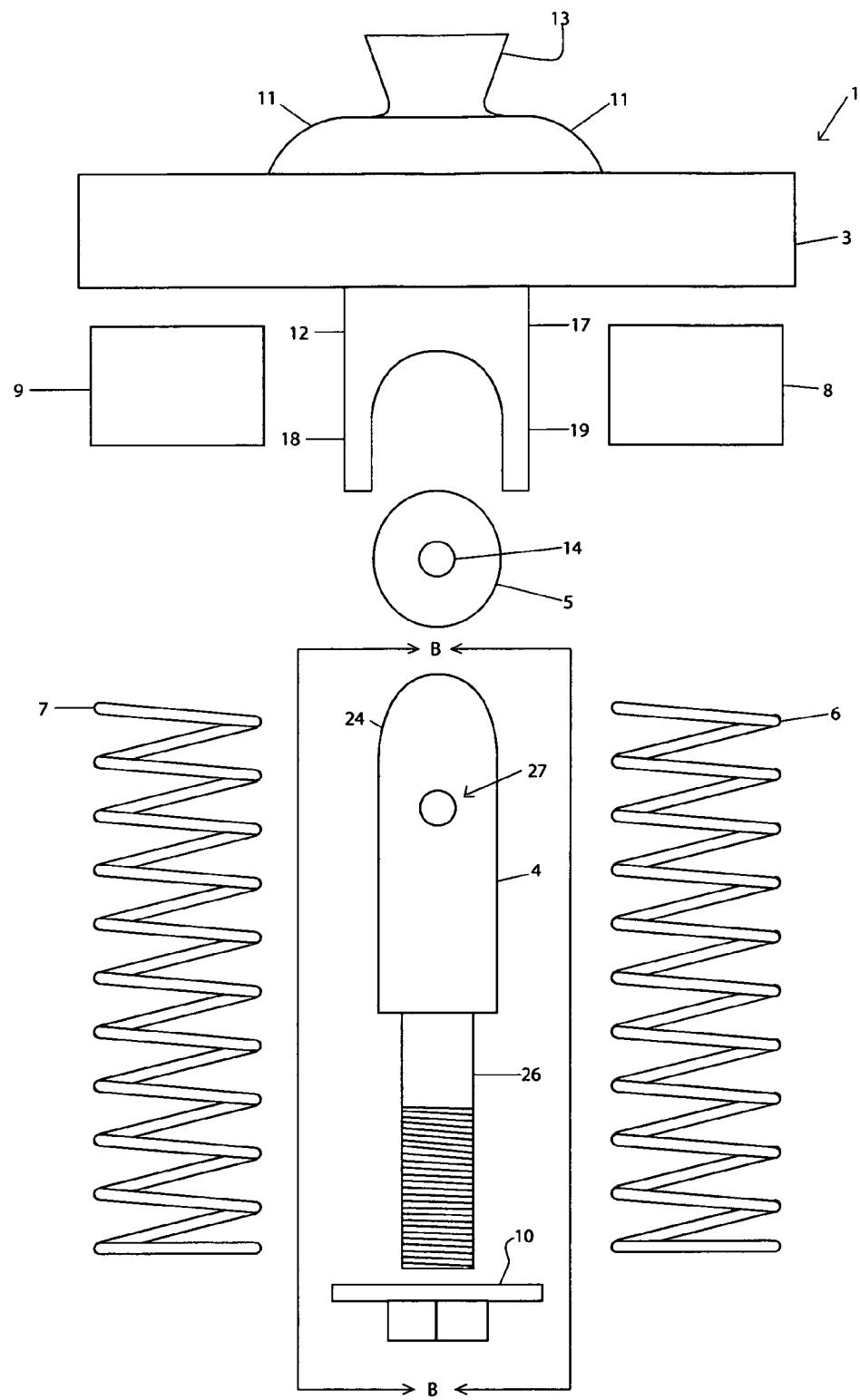
FIG. 3 is an exploded view of the artificial ankle shown in FIG. 1 and illustrates the components of the artificial ankle.

As shown in FIGS. 1, 2 and 3, artificial ankle 1 is comprised of bridge 3, clevis 4, ball joint 5, coil spring 6, coil spring 7, sleeve 8, sleeve 9 and flange-nut 10.

Bridge 3 is a plate having dome 11 extending upwardly from the top side of the plate, and shackle 12 extending downwardly from the bottom side of the plate. Boss 13 projects upwardly from the top of dome 11.

Bridge 3 further includes pocket 8a, formed in the bottom front of bridge 3, and pocket 9a formed in the bottom rear of bridge 3. Pockets 8a and 9a are centered on the longitudinal axis of bridge 3. Each of pockets 8a and 9a is a hole, wherein the diameter and depth of each of pockets 8a and 9a are identical.

The outside diameters of each of sleeves 8 and 9 are sized to permit each sleeve to be slidably inserted into each pocket 8a and 9a, respectively, and preferably to produce a friction fit between the wall of each pocket and the outside wall of each sleeve.

As seen in FIGS. 1, 2, 5, 6 and 7, boss 13, shackle 12, ball joint 5 and clevis 4 are in vertical alignment in both the sagittal and frontal planes, which are referred to herein as the first vertical plane and the second vertical plane, respectively. Boss 13 is in the shape of a truncated pyramid and has been referred to in the art as a pyramid.

The mentioned horizontal plane passes through the center of ball joint 5, and intersects each of the first and second vertical planes which also pass through the center of ball joint 5. The intersection of the first vertical plane and the second vertical plane is a vertical line which passes through the center of ball joint 5. The intersection of the horizontal plane and the second vertical plane is the first horizontal axis. The intersection of the horizontal plane and the first vertical plane is the second horizontal axis. The mentioned first and second horizontal axes are perpendicular each to the other and intersect at the center of ball joint 5. Each horizontal axis serves as an axis of rotation around which clevis 4 rotates to produce plantar flexion, dorsiflexion, eversion and inversion.

Figure 4:
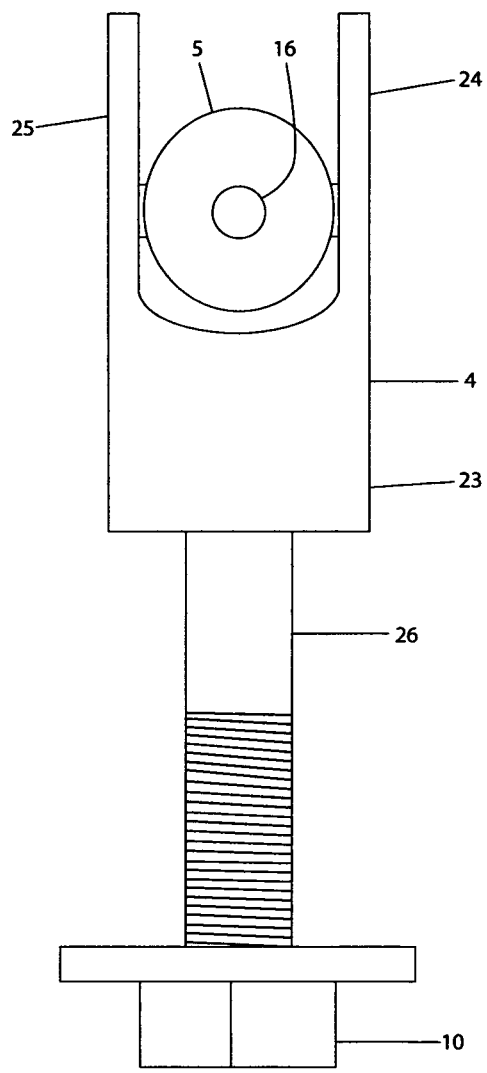
FIG. 4 is taken in the direction of lines B-B of FIG. 3.

Axial holes are drilled into ball 5 along each of the first and second horizontal axes. Each such hole can pass completely through ball 5 or only partly through ball 5. FIG. 2 shows axial holes 14 and 15 drilled into ball joint 5 along the first horizontal axis, and FIG. 3 shows axial hole 14 drilled into ball joint 5 along the first horizontal axis. Axial holes 14 and 15, as shown in FIG. 2, do not pass completely through ball joint 5. FIGS. 1, 2 and 4 show axial hole 16 drilled into ball joint 5 along the second horizontal axis. Axial hole 16 does pass completely through ball 5.

As seen in FIGS. 1 and 3, shackle 12 comprises base 17, which abuts the bottom of bridge 3, and ears 18 and 19 which extend downwardly from base 17. Horizontal hole 20 extends completely through ear 18 and horizontal hole 21 extends completely through ear 19. Holes 20 and 21 are in alignment with hole 16 in ball joint 5. Each of holes 20 and 21 contain internal threads. Hole 16 is not threaded. First axle 22 extends through holes 20, 16 and 21. First axle 22 is threadedly attached to holes 20 and 21, but is not attached to hole 16. Accordingly, bridge 3 is permitted to rotate around first axle 22 in the mentioned frontal plane to enable eversion and inversion motion.

As seen in FIGS. 2 and 4, clevis 4 comprises base 23, arm 24, arm 25 and tang 26. Horizontal hole 27 extends completely through arm 24 and horizontal hole 28 extends completely through arm 25. Holes 27 and 28 are in alignment with holes 14 and 15 in ball joint 5. Each of holes 27 and 28 contain internal threads. Holes 14 and 15 are not threaded. Second axle 29a extends through holes 27 and 14 and second axle 29b extends through holes 28 and 15. Second axle 29a is threadedly attached to hole 27, but is not attached to hole 14. Second axle 29b is threadedly attached to hole 28, but is not attached to hole 15. Accordingly, clevis 4 is permitted to rotate around second axle 29a-29b in the mentioned sagittal plane to enable plantar flexion and dorsiflexion.

As can be seen in FIG. 2, arms 24 and 25 of clevis 4 extend above the lowest part of base 17 of shackle 12. Accordingly, the extent of rotation of bridge 3 around first axle 22 (or expressed differently, the rotation of shackle 12 around first axle 22) is controlled by the distance between the inside of arm 24 and the near side of base 17 of shackle 12, and the distance between the inside of arm 25 and the near side of base 17 of shackle 12. Base 17 of shackle 12 thus limits rotation of shackle 12 around first axle 22 because it contacts arms 24 and 25 of clevis 4. Similarly, as see in FIG. 5, the extent of rotation of clevis 4 around second axle 29a-29b is controlled by the length of ears 18 and 19 of shackle 12. In this regard, ears 18 and 19 of shackle 12 upon rotation of clevis 4 contacts base 23 of clevis 4. Ears 18 and 19 of shackle 12 thus limits rotation of clevis 4 around second axle 29a-29b.

FIGS. 1 and 2 include side and end vertical section views, respectively, of an artificial jointless foot 2 comprised of upper portion 30, lower portion 31, and flexible covering 32. Upper portion 30 is an incompressible wooden core, lower portion 31 is a solid, compressible cast resin and flexible covering 32 is a water proof elastomeric material. An example of an artificial jointless foot useful herein is available from Otto Bock, a German Company, under the trademark Pedilan® light foot. The example foot is modified for connection to the artificial ankle of this invention.

Surface 33 of upper portion 30 is parallel, in the neutral position as shown in FIG. 1, to the ground surface and to bridge 3 of ankle 1. Projections 34 and 35 are solid cylinders which are rigidly attached to the bottoms of holes 36 and 37 which are drilled in upper portion 30 from surface 33. Projections 34 and 35 extend above surface 33. The distance from the bottom of hole 36 to the bottom of sleeve 9 is equal to the distance from the bottom of hole 37 to the bottom of sleeve 8.

The materials of construction and the design features of springs 6 and 7 are identical and springs 6 and 7 are equal in length and diameter. The diameters of holes 36 and 37 are sized to permit slidable insertion therein of springs 7 and 6, respectively. The diameters of projections 34 and 35 are sized to permit longitudinal insertion of the projections into the respective interiors of springs 6 and 7. The longitudinal axis of hole 36 and the longitudinal axis of sleeve 9 coincide, and the longitudinal axis of hole 37 and the longitudinal axis of sleeve 8 coincide. Sleeve 8, hole 37 and projection 34 cooperate to maintain spring 6 in operating position, and sleeve 9, hole 36 and projection 35 cooperate to maintain spring 7 in operating position.

Figure 8:
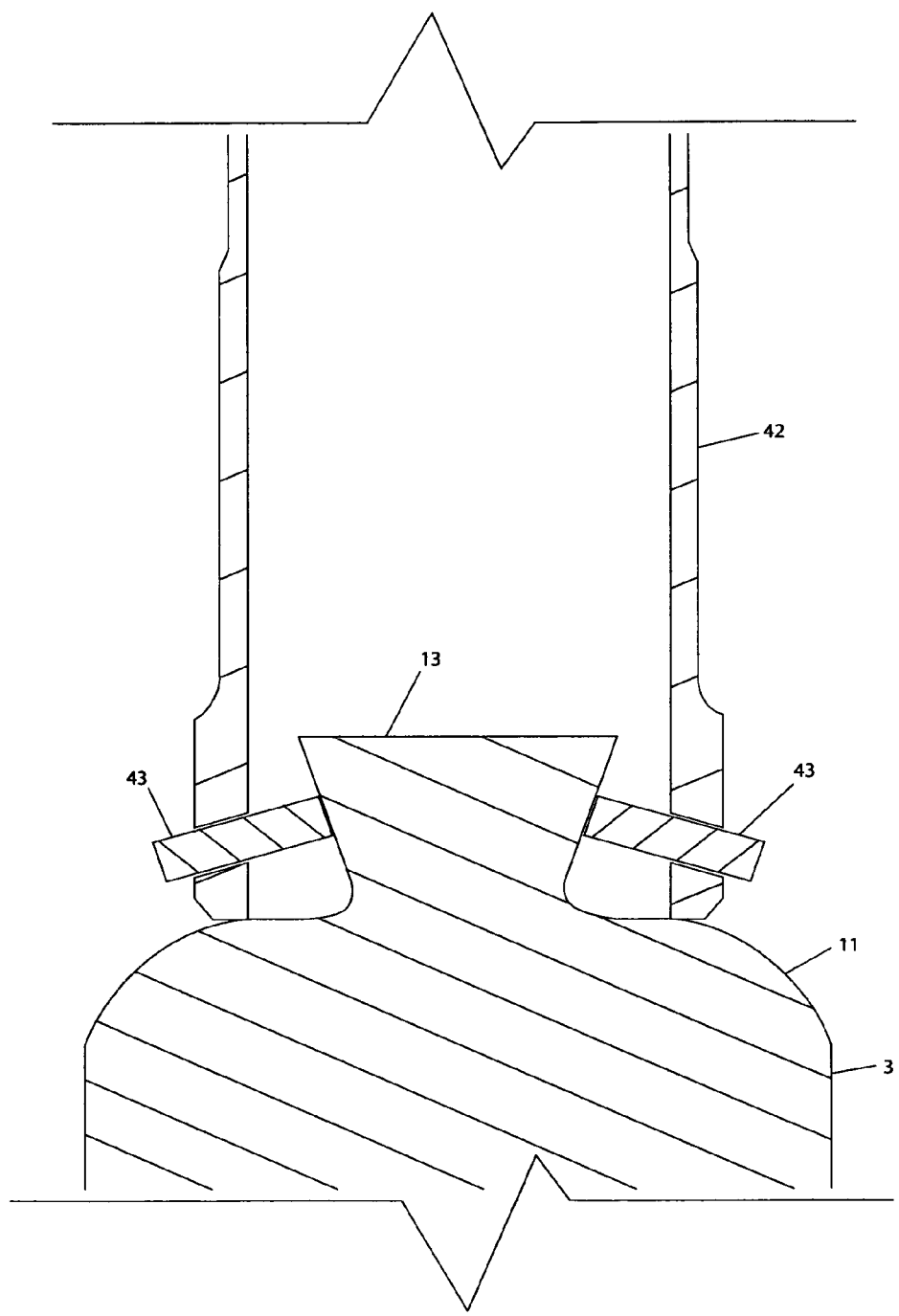
FIG. 8 is a sectional view of the connection of the artificial ankle of this invention to the pylon.

Given the existence of the conditions recited in the two preceding paragraphs, it is believed that, in the neutral position, pylon 42, as shown in FIG. 8, will be perpendicular to the ground surface after it has been attached to pyramid 13 and after artificial ankle 1 has been attached to artificial foot 2. Attachment of artificial ankle 1 to artificial foot 2 and attachment of pylon 42 to pyramid 13 is disclosed below.

Plate 38 is rigidly imbedded within upper portion 30 of artificial foot 2. Hole 39 is drilled in upper portion 30 from surface 33 to plate 38. Hole 39 is rectangular in shape and is sized to slidably receive base 23 of clevis 4. As shown in FIGS. 1 and 3, the width of hole 39 is equal to or slightly greater than the distance from the inside of ear 18 of shackle 12 to the inside of ear 19 of shackle 12, and is less than the distance from the outside of ear 18 to the outside of ear 19. Accordingly, the depth of any slidable penetration of base 23 of clevis 4 into hole 39 is limited by contact between surface 33 and the bottoms of ears 18 and 19 of shackle 12.

Circular hole 40 is drilled through plate 38. The diameter of hole 40 is sized to enable tang 26 of clevis 4 to pass there through. Each of the length and width dimensions of hole 39 is greater than the diameter of hole 40.

Circular hole 41 is drilled from the bottom of artificial foot 2 through flexible covering 32, lower portion 31 and partially through upper portion 30 to plate 38. The diameter of hole 41 is greater than the diameter of flange-nut 10 by an amount sufficient to enable flange-nut 10 to be placed in hole 41 against the bottom side of plate 38 and to enable flange-nut 10 to be threaded to tang 26 of clevis 4. The vertical axes of holes 39, 40 and 41 are coincident.

Artificial ankle 1 and artificial foot 2 are assembled by first assembling the elements shown in FIG. 3 to form the component shown in FIG. 5. Thereafter, tang 26 of clevis 4 is positioned for insertion into hole 40 and projections 34 and 35 are inserted into the respective interiors of springs 6 and 7. Thereafter, force is exerted against bridge 3 to compress springs 6 and 7 by an amount sufficient to enable tang 26 to pass through hole 40, and the applied force is maintained for a time sufficient to permit threaded attachment of flange-nut 10 to tang 26.

Finally, pylon 42 is positioned over pyramid 13 as shown in FIG. 8. Pylon 42 is preferably a cylindrical metal tube such as model 2R49 CE available from Otto Bock. Upon being positioned as shown, pins 43, which are threaded in pylon 42, are tightened against each of the four sides of pyramid 13.

The entire assembly is then connected to the user as is known in the art.

In operation, the ability of artificial foot 2 to produce plantar flexion, dorsiflexion, inversion, eversion and body weight dispersion is a function of the flexibility of artificial ankle 1. In this regard the flexibility of artificial ankle 1 is believed to be controlled by the degree of compression of springs 6 and 7, wherein the greater the compression the less the flexibility. Accordingly, spring compression and artificial ankle flexibility are inversely related. The extent of compression loaded in springs 6 and 7 is controlled by tension in tang 26 which is adjusted by tightening and loosening flange-nut 10. A user can accordingly control ankle flexibility by adjusting flange-nut 10.

In addition to artificial ankle flexibility discussed above, which enables movement of the artificial foot in the mentioned sagittal and coronal planes, movement of the artificial foot in the horizontal plane can be controlled by the relative sizes of the base 23 of clevis 4 and rectangular hole 39 in upper portion 30 of artificial foot 2. If the dimensions of base 23 and hole 39 are substantially the same, then horizontal rotation of ankle 1 is very limited if not prevented. However, increasing the dimensions of hole 39 relative to the dimensions of base 23, will permit horizontal rotation ankle 1. A user can accordingly adjust such movement as desired.

Having described the invention that which is claimed is:

1. An artificial ankle for attachment to an artificial foot and an artificial leg bone, said artificial ankle comprising a universal joint, a shackle, a clevis, a bridge, a first spring and a second spring, said universal joint is a ball positioned intermediate said shackle and said clevis, wherein said shackle is rotatably attached to said ball by a first axle and said clevis is rotatably attached to said ball by a second axle, wherein said first axle and said second axle lie in the same plane and said first axle is perpendicular to said second axle, said artificial ankle is positioned between said artificial foot and said artificial leg bone, and said clevis includes a tang for slidably connecting said artificial ankle to said artificial foot.

2. The artificial ankle of claim 1 wherein said bridge has a top side and a bottom side, said bottom side of said bridge includes a first pocket and a second pocket and said shackle is rigidly attached to said bottom side of said bridge intermediate said first pocket and said second pocket.

3. The artificial ankle of claim 2 wherein said first spring has a first end and a second end and said second spring has a first end and a second end, wherein said first pocket is adapted to receive said first end of said first spring and said second pocket is adapted to receive said first end of said second spring.

4. The artificial ankle of claim 3 wherein said artificial foot has a top side and a bottom side, wherein said top side of said artificial foot is adapted to receive said second end of said first spring in a first location and is adapted to receive said second end of said second spring in a second location wherein said first spring and said second spring are positioned intermediate said bottom side of said bridge and said top side of said artificial foot.

5. The artificial ankle of claim 4 wherein said top side of said bridge includes a boss for connecting said bridge to said artificial leg bone.

6. The artificial ankle of claim 5 wherein said artificial leg bone is a pylon, wherein said pylon is connected to said boss.

7. An artificial ankle for attachment to an artificial foot and an artificial leg bone, said artificial ankle being useful to enable said artificial foot to distribute vertically applied weight of a human body to ground, and useful to enable plantar flexion, dorsiflexion, eversion and inversion of said artificial foot, said artificial ankle being comprised of a universal joint, a shackle, a clevis, a bridge, a first spring and a second spring wherein:

said bridge has a top side and a bottom side, said top side of said bridge includes a boss for connecting said bridge to said artificial leg bone, said bottom side of said bridge includes the shackle rotatably connected to said universal joint and includes a first pocket for receiving said first spring and a second pocket for receiving said second spring, said clevis is rotatably connected to said universal joint and includes a tang for slidably connecting said clevis to said artificial foot, and said universal joint is a ball wherein said shackle is connected to said ball by a first axle and said clevis is rotatably connected to said ball by a second axle, wherein said first axle and said second axle lie in the same plane and said first axle is perpendicular to said second axle.

8. The artificial ankle of claim 7 wherein said first spring has a first end and a second end, and said second spring has a first end and a second end.

9. The artificial ankle of claim 8 wherein said first pocket is adapted to receive said first end of said first spring, and said second pocket is adapted to receive said first end of said second spring, and said shackle is positioned intermediate said first pocket and said second pocket.

10. The artificial ankle of claim 9 wherein said artificial leg bone is a pylon and said pylon is connected to said boss.

11. The artificial ankle of claim 10 wherein said artificial foot has a top side and a bottom side, wherein said top side of said artificial foot is adapted to receive said second end of said first spring in a first location and is adapted to receive said second end of said second spring in a second location wherein said first spring and said second spring are positioned intermediate said bottom side of said bridge and said top side of said artificial foot.

\* \* \* \* \*